(12) United States Patent
Rossetto et al.

(10) Patent No.: US 11,779,192 B2
(45) Date of Patent: Oct. 10, 2023

(54) MEDICAL IMAGE VIEWER CONTROL FROM SURGEON'S CAMERA

(71) Applicant: COVIDIEN LP, Mansfield, MA (US)

(72) Inventors: Francesca Rossetto, Longmont, CO (US); Joe D. Sartor, Longmont, CO (US)

(73) Assignee: COVIDIEN LP

( * ) Notice: Subject to any disclaimer, the term of this patent is extended or adjusted under 35 U.S.C. 154(b) by 423 days.

(21) Appl. No.: 15/585,592

(22) Filed: May 3, 2017

(65) Prior Publication Data

US 2018/0317740 A1    Nov. 8, 2018

(51) Int. Cl.
*A61B 1/00*   (2006.01)
*A61B 1/05*   (2006.01)
(Continued)

(52) U.S. Cl.
CPC ........ *A61B 1/00009* (2013.01); *A61B 1/0005* (2013.01); *A61B 1/00006* (2013.01);
(Continued)

(58) Field of Classification Search
CPC ............ A61B 1/00006; A61B 1/00009; A61B 1/0005; A61B 1/3132; A61B 2034/302; A61B 2090/365; A61B 2090/373; A61B 2034/105; A61B 2090/367; A61B 2034/2065; A61B 34/20; A61B 90/37; A61B 5/062; A61B 1/307; A61B 1/2676; A61B 1/05; A61B 1/00149; A61B 34/30; A61B 2017/00809; A61B 2034/2051; A61B 2034/2059; A61B 1/00195; H04N 13/204; H04N 5/23293; H04N 2005/2255; H04N 23/555
See application file for complete search history.

(56) References Cited

U.S. PATENT DOCUMENTS 6,188,355 B1    2/2001   Gilboa
8,267,853 B2    9/2012   Fisher et al.
(Continued)

FOREIGN PATENT DOCUMENTS

EP    0920838 A2    6/1999

OTHER PUBLICATIONS

Langø, T. et al. "Navigation in laparoscopy—Prototype research platform for improved image-guided surgery", Minimally Invasive Therapy, vol. 17, No. 1, Nov. 29, 2007, pp. 17-33 (Year: 2007).*
(Continued)

*Primary Examiner* — Ryan N Henderson
(74) *Attorney, Agent, or Firm* — Carter, DeLuca & Farrell LLP (57) ABSTRACT

Provided in accordance with the present disclosure are systems, devices, and methods for displaying medical images based on a location of a camera. In an exemplary embodiment, a method includes receiving image data of a patient's body, identifying an organ in the image data, generating a three-dimensional (3D) model of at least a portion of the patient's body based on the image data, registering the 3D model with the patient's body, determining a location of a camera inside the patient's body, identifying a 2D slice image from the image data based on the determined location of the camera inside the patient's body, and displaying the 2D slice image.

5 Claims, 4 Drawing Sheets

(51) Int. Cl.

| | |
|---|---|
| *A61B 1/267* | (2006.01) |
| *A61B 1/307* | (2006.01) |
| *A61B 1/313* | (2006.01) |
| *A61B 90/00* | (2016.01) |
| *A61B 34/20* | (2016.01) |
| *A61B 34/30* | (2016.01) |
| *A61B 5/06* | (2006.01) |
| *H04N 23/50* | (2023.01) |

(52) U.S. Cl.
CPC .... *A61B 1/000095* (2022.02); *A61B 1/00149* (2013.01); *A61B 1/05* (2013.01); *A61B 1/2676* (2013.01); *A61B 1/307* (2013.01); *A61B 1/3132* (2013.01); *A61B 5/062* (2013.01); *A61B 34/20* (2016.02); *A61B 34/30* (2016.02); *A61B 90/37* (2016.02); *A61B 2034/2051* (2016.02); *A61B 2034/302* (2016.02); *A61B 2090/365* (2016.02); *A61B 2090/367* (2016.02); *H04N 23/555* (2023.01)

(56) References Cited

U.S. PATENT DOCUMENTS

| | | | | |
|---|---|---|---|---|
| 8,554,307 | B2 | 10/2013 | Razzaque et al. | |
| 8,585,598 | B2* | 11/2013 | Razzaque | A61B 90/37 600/439 |
| 9,901,406 | B2* | 2/2018 | State | G06T 19/00 |
| 10,188,467 | B2* | 1/2019 | Razzaque | A61B 90/37 |
| 10,820,946 | B2* | 11/2020 | Heaney | A61B 34/20 |
| 11,534,245 | B2* | 12/2022 | Heaney | A61B 90/37 |
| 2002/0009215 | A1* | 1/2002 | Armato | G06K 9/38 382/131 |
| 2003/0099385 | A1* | 5/2003 | Zeng | G06T 7/0012 382/128 |
| 2006/0258938 | A1* | 11/2006 | Hoffman | A61B 1/00193 600/424 |
| 2007/0021738 | A1* | 1/2007 | Hasser | A61B 90/37 606/1 |
| 2008/0071140 | A1* | 3/2008 | Gattani | A61B 34/20 600/117 |
| 2008/0071141 | A1* | 3/2008 | Gattani | A61B 5/065 600/117 |
| 2008/0071142 | A1* | 3/2008 | Gattani | G16H 40/63 600/117 |
| 2008/0071143 | A1* | 3/2008 | Gattani | A61B 5/061 600/117 |
| 2008/0118135 | A1* | 5/2008 | Averbuch | G06T 15/08 382/131 |
| 2008/0175463 | A1* | 7/2008 | Strommer | G06K 9/6201 382/131 |
| 2009/0318756 | A1* | 12/2009 | Fisher | A61B 1/04 600/109 |
| 2010/0121190 | A1* | 5/2010 | Pagoulatos | A61B 8/00 600/437 |
| 2011/0085720 | A1* | 4/2011 | Averbuch | A61B 90/36 382/131 |
| 2011/0158488 | A1* | 6/2011 | Cohen | A61B 34/20 382/128 |
| 2011/0251483 | A1* | 10/2011 | Razzaque | A61B 6/466 600/424 |
| 2012/0069167 | A1* | 3/2012 | Liu | A61B 6/584 348/65 |
| 2013/0197357 | A1* | 8/2013 | Green | A61B 8/0841 600/424 |
| 2013/0250081 | A1* | 9/2013 | Pandey | A61B 90/37 348/77 |
| 2014/0088357 | A1* | 3/2014 | Ikuma | A61B 1/00009 600/109 |
| 2014/0303491 | A1* | 10/2014 | Shekhar | A61B 8/4209 600/424 |
| 2015/0138329 | A1* | 5/2015 | Braun | A61B 1/0005 348/71 |
| 2015/0287236 | A1* | 10/2015 | Winne | G06F 3/147 382/128 |
| 2015/0335303 | A1* | 11/2015 | Chandelier | A61B 6/466 345/427 |
| 2016/0000302 | A1* | 1/2016 | Brown | A61B 6/5247 600/103 |
| 2016/0000356 | A1* | 1/2016 | Brown | A61B 5/064 600/424 |
| 2016/0000517 | A1* | 1/2016 | Ke | A61B 34/20 600/103 |
| 2016/0005193 | A1 | 1/2016 | Markov et al. | |
| 2016/0038248 | A1 | 2/2016 | Bharadwaj et al. | |
| 2016/0166336 | A1* | 6/2016 | Razzaque | A61B 34/20 606/130 |
| 2016/0317229 | A1 | 11/2016 | Girotto et al. | |
| 2016/0324585 | A1* | 11/2016 | Noonan | A61B 90/37 |
| 2017/0105802 | A1* | 4/2017 | Taraschi | A61B 34/20 |
| 2018/0116731 | A1* | 5/2018 | State | A61B 90/37 |
| 2019/0008595 | A1* | 1/2019 | Popovic | A61B 34/20 |

OTHER PUBLICATIONS

Extended European Search Report issued in Appl. No. EP 18170432.1 dated Oct. 1, 2018 (8 pages).

Langø, T. et al. "Navigation in laparoscopy—Prototype research platform for improved image-guided surgery", Minimally Invasive Therapy, vol. 17, No. 1, Nov. 29, 2007, pp. 17-33.

European Examination Report issued in corresponding application EP 18170432.1 dated May 18, 2021 (5 pages).

European Examination Report issued in corresponding application EP 18 170 432.1 dated May 22, 2023 (4 pages).

* cited by examiner

MEDICAL IMAGE VIEWER CONTROL FROM SURGEON'S CAMERA

BACKGROUND

Technical Field

The present disclosure relates to tools for assisting surgeons during the performance of medical procedures, and more particularly, to systems, devices, and methods for controlling images displayed by a medical image viewer based on movement of surgical tools.

Description of Related Art

Surgical procedures are commonly used to diagnose and treat diseases occurring inside a patient's body. While traditional open surgical procedures provided surgeons both access to and a view of a surgical site, modern surgical techniques, such as endoscopic, laparoscopic, and robotic surgical procedures do not provide surgeons with the same view of the surgical site. Minimally invasive surgical procedures, such as endoscopic and laparoscopic procedures, are often preferred by patient's and surgeons to speed the patients' recovery post-surgery. The success of a surgical procedure often depends on the surgeon's ability to visualize the surgical site. However, visualization of the surgical site during such minimally invasive surgical procedures is limited. As such, improvements are needed in pre-operative and live imaging techniques techniques for use during minimally invasive surgical procedures. Systems and methods for improvements in visualizing a surgical site during a surgical procedure are described hereinbelow.

SUMMARY

Provided in accordance with an embodiment of the present disclosure is a method of displaying medical images based on a location of a camera. In an aspect of the present disclosure, the method includes receiving image data of a patient's body, identifying an organ in the image data, generating a three-dimensional (3D) model of at least a portion of the patient's body based on the image data, registering the 3D model with the patient's body, determining a location of a camera inside the patient's body, identifying a 2D slice image from the image data based on the determined location of the camera inside the patient's body, and displaying the 2D slice image.

In another aspect of the present disclosure, the camera is coupled to an electromagnetic sensor, and the location of the camera inside the patient's body is determined based on a tracked position of the electromagnetic sensor inside the patient's body.

In yet another aspect of the present disclosure, the camera is coupled to a surgical robot.

In a further aspect of the present disclosure, the location of the camera inside the patient's body is determined based on a pose of the surgical robot.

In another aspect of the present disclosure, the determined location of the camera inside the patient's body is a first location of the camera inside the patient's body and the 2D slice image is a first 2D slice image, and the method further includes determining a second location of the camera inside the patient's body after the camera has been moved, identifying a second 2D slice image from the image data based on the determined second location of the camera, and displaying the second 2D slice image.

In a further aspect of the present disclosure, the method further includes determining a direction of movement of the camera based on the first and second locations of the camera, and the second 2D slice image is identified based on the determined second location of the camera and further based on the determined direction of movement of the camera.

In yet a further aspect of the present disclosure, identifying the 2D slice image includes generating a 2D slice image in an orientation based on the direction of movement of the camera.

In still a further aspect of the present disclosure, the 2D slice image is generated in an orientation that is non-orthogonal.

In another aspect of the present disclosure, the organ is the patient's lungs, and the 3D model includes a model of the patient's lungs wherein deflation of at least a portion of the patient's lungs has been simulated.

In yet another aspect of the present disclosure, identifying the 2D slice image includes generating a 2D slice image in an axial, sagittal, or coronal orientation.

In still another aspect of the present disclosure, the organ is at least one of a lung, a kidney, a spleen, a prostate, a thyroid, and a liver.

Provided in accordance with an embodiment of the present disclosure is a system for displaying medical images based on a location of a camera. In an aspect of the present disclosure, the system includes a laparoscopic camera, a display device, and a computing device including a processor and a memory storing instructions which, when executed by the processor, cause the computing device to receive image data of the patient's body, identify an organ in the image data, generate a three-dimensional (3D) model of at least a portion of the patient's body based on the image data, register the 3D model with the patient's body, identify a 2D slice image from the image data based on a determined location of the laparoscopic camera inside the patient's body, and cause the display device to display the 2D slice image.

In another aspect of the present disclosure, the laparoscopic camera is coupled to an electromagnetic sensor, and the system further includes an electromagnetic tracking system configured to determine the location of the laparoscopic camera inside the patient's body based on a tracked position of the electromagnetic sensor inside the patient's body.

In yet another aspect of the present disclosure, the system further includes a surgical robot, the laparoscopic camera is coupled to the surgical robot, and the location of the laparoscopic camera inside the patient's body is determined based on a pose of the surgical robot.

In still another aspect of the present disclosure, the determined location of the laparoscopic camera inside the patient's body is a first location of the laparoscopic camera inside the patient's body and the 2D slice image is a first 2D slice image, the electromagnetic tracking system is further configured to determine a second location of the laparoscopic camera inside the patient's body after the laparoscopic camera has been moved, and the instructions, when executed by the processor, further cause the computing device to identify a second 2D slice image from the image data based on the determined second location of the laparoscopic camera, and cause the display device to display the second 2D slice image.

In a further aspect of the present disclosure, the instructions, when executed by the processor, further cause the computing device to determine a direction of movement of the laparoscopic camera based on the first and second locations of the laparoscopic camera, and the second 2D slice image is identified based on the determined second location of the laparoscopic camera and further based on the determined direction of movement of the laparoscopic camera.

In yet a further aspect of the present disclosure, identifying the 2D slice image includes generating a 2D slice image in an orientation based on the direction of movement of the laparoscopic camera.

In still a further aspect of the present disclosure, the 2D slice image is generated in an orientation that is non-orthogonal.

In another aspect of the present disclosure, the organ is the patient's lungs, and the 3D model includes a model of the patient's lungs wherein deflation of at least a portion of the patient's lungs has been simulated.

In yet another aspect of the present disclosure, the organ is at least one of a lung, a kidney, a spleen, a prostate, a thyroid, and a liver.

Provided in accordance with an embodiment of the present disclosure is a non-transitory computer-readable storage medium storing a program for displaying medical images based on a location of a camera. In an aspect of the present disclosure, the program includes instructions which, when executed by a processor, cause a computing device to receive image data of a patient's body, identify an organ in the image data, generate a three-dimensional (3D) model of at least a portion of the patient's body based on the image data, register the 3D model with the patient's body, determine a location of a camera inside the patient's body, identify a 2D slice image from the image data based on the determined location of the camera, and cause a display device to display the 2D slice image.

In another aspect of the present disclosure, the camera is coupled to an electromagnetic sensor, and the location of the camera inside the patient's body is determined based on a tracked position of the electromagnetic sensor inside the patient's body.

In yet another aspect of the present disclosure, the camera is coupled to a surgical robot.

In a further aspect of the present disclosure, the location of the camera inside the patient's body is determined based on a pose of the surgical robot.

In another aspect of the present disclosure, the determined location of the camera inside the patient's body is a first location of the camera inside the patient's body and the 2D slice image is a first 2D slice image, and the instructions, when executed by the processor, further cause the computing device to determine a second location of the camera inside the patient's body after the camera has been moved, identify a second 2D slice image from the image data based on the determined second location of the camera, and cause the display device to display the second 2D slice image.

In a further aspect of the present disclosure, the instructions, when executed by the processor, further cause the computing device to determine a direction of movement of the camera based on the first and second locations of the camera, and the second 2D slice image is identified based on the determined second location of the camera and further based on the determined direction of movement of the camera.

In yet a further aspect of the present disclosure, identifying the 2D slice image includes generating a 2D slice image in an orientation based on the direction of movement of the camera.

In still a further aspect of the present disclosure, the 2D slice image is generated in an orientation that is non-orthogonal.

In another aspect of the present disclosure, the organ is the patient's lungs and the 3D model includes a model of the patient's lungs wherein deflation of at least a portion of the patient's lungs has been simulated.

In yet another aspect of the present disclosure, identifying the 2D slice image includes generating a 2D slice image in an axial, sagittal, or coronal orientation.

In still another aspect of the present disclosure, the organ is at least one of a lung, a kidney, a spleen, a prostate, a thyroid, and a liver.

Any of the above aspects and embodiments of the present disclosure may be combined without departing from the scope of the present disclosure.

BRIEF DESCRIPTION OF THE DRAWINGS

Various aspects and features of the present disclosure are described hereinbelow with references to the drawings, wherein.

DETAILED DESCRIPTION

The present disclosure relates to devices, systems, and methods for controlling images displayed by a medical image viewer based on movement of surgical tools. More particularly, the disclosure relates to tracking a location and direction of movement of surgical tools, such as laparoscopes (although other tools could also be used), and selecting and displaying, via a medical image viewer such as a display device, medical images based on the location and direction of movement of the surgical tool.

The tracking of the location and direction of movement of the surgical tools may be performed using an electromagnetic tracking system, and the selection and display of the medical images may be performed by one or more software applications executing on a computer connected to the display device. The software applications may, for example, generate a three-dimensional (3D) model or map of the patient's body based on radiographically obtained image data, such as CT image data, to use for the visual representation of the patient's body. For example, in an embodiment where the systems and methods of the present disclosure are used in thoracic surgery, the 3D model may show, among other things, the airways, vascular and lymphatic lumens and structures, pleura, fissures and other structures of the patient's lungs, and other organs and structures in and around the patient's thoracic cavity.

In other embodiments, the systems and methods of the present disclosure may be used for various other forms of surgery, including abdominal surgery, joint surgery, etc. Further details about systems, devices, and methods for obtaining image data for, and creation of, a deflated 3D model are provided in commonly-owned co-pending U.S. Provisional Patent Application No. 62/315,773, entitled "THORACIC ENDOSCOPE FOR SURFACE SCANNING", filed on Mar. 31, 2016, by Sartor et al., and commonly-owned co-pending U.S. Provisional Patent Application No. 62/369,986, entitled "SYSTEM AND METHOD OF USING AN ENDOSCOPIC CATHETER AS A PORT IN LAPAROSCOPIC SURGERY", filed on Aug. 2, 2016, by William S. Krimsky, the entire contents of both of which are incorporated herein by reference. By using CT image data collected while the patient's lungs are inflated, e.g. at breath-hold, and when the patient's lungs are deflated, the 3D model may be used to visualize the patient's lungs at different states of inflation. Further, the 3D model may also show the bronchial, vascular, and lymphatic structures and lumens inside the patient's lungs and how such lumens move during the breathing cycle.

The systems, devices, methods, and computer-readable media described herein are useful for medical procedures, such as diagnostic and/or treatment procedures, performed on the patient's lungs and surrounding tissue, as well as other areas of the patient's body, including, for example, the kidneys, the spleen, the prostate, the thyroid, the liver, etc. For example, in an embodiment where a clinician is performing treatment of an area of the patient's lungs, the methods and systems may provide the clinician with various views, including live images from one or more laparoscopes, one or more views of the 3D model, and one or more medical images, such as CT images, obtained preoperatively or intra-operatively and selected for display based on a tracked location and direction of movement of a surgical tool used during the treatment procedure. These and other aspects of the present disclosure are detailed hereinbelow.

Methods for planning and performing diagnostic and/or treatment procedures in a patient's body may be implemented via an electromagnetic navigation (EMN) system. Generally, in an embodiment, the EMN system may be used in navigating and positioning a variety of tools to one or more treatment locations, such as a surgical site, within a patient's body. The EMN system may be configured to display various views of the patient's body, and of the aforementioned 3D model.

EMN offers a streamlined method of tracking sensors coupled to surgical instruments and/or cameras, and the system would work equally well by any means of locational tracking, whether wired or wireless EMN. Additionally, those skilled in the art will recognize that other methods of tracking surgical instruments and/or cameras, such as optical positioning using reflectors or active light emitting diodes (LED), as performed by Northern Digital Inc., as well as 3D scanning may also be used without departing from the scope of the present disclosure. Various EM tracking systems may be used depending on the tools used during the procedure. For example, some tools may be constructed of materials, such as stainless steel, that can cause distortions in the EM field that are too severe to accurately identify sensors coupled to or proximate such tools, and thus EMN tracking systems that are designed to compensate for such distortions may be preferred. An example of such an EM tracking system is the AURORA™ system sold by Northern Digital Inc., which is further described in commonly-owned co-pending U.S. Patent Application Publication No. 2016/0317229, entitled METHODS FOR MICROWAVE ABLATION PLANNING AND PROCEDURE, filed on Apr. 15, 2016, by Girotto et al., the entire contents of which are incorporated herein by reference.

Figure 1:
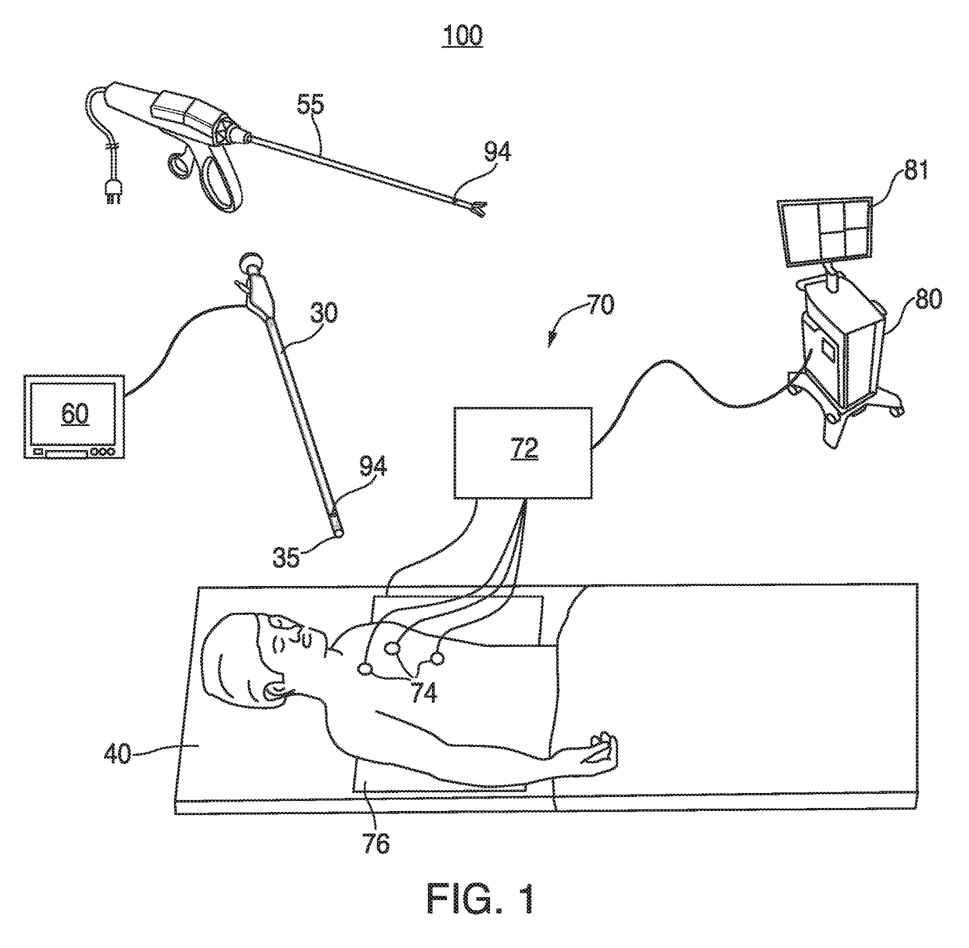
FIG. 1 is a schematic diagram of a laparoscopic system for planning and performing diagnostic and/or treatment procedures in a patient's body, according to an embodiment of the present disclosure.

With reference to FIG. 1, a system 100 suitable for performing laparoscopic surgery on a patient is provided in accordance with an embodiment of the present disclosure. As shown in FIG. 1, system 100 is used to perform one or more diagnostic and/or treatment procedures on a patient supported on an operating table 40. In this regard, system 100 generally includes at least one laparoscope 30, at least one surgical tool 55, monitoring equipment 60, an electromagnetic (EM) tracking system 70, and a computing device 80. In some embodiments, system 100 may further include a surgical robot (not shown) including one or more robotic arm assemblies and a controller configured to operate the surgical robot. In such embodiments, laparoscope 30 and/or surgical tool 55 may be coupled to the surgical robot via at least one of the robotic arm assemblies.

Laparoscope 30 includes a source of illumination and a laparoscopic camera 35 coupled to monitoring equipment 60, for example, a video display, for displaying video images received from camera 35. Laparoscope 30 is configured for insertion into the patient's body, e.g. through a surgical incision and/or a laparoscopic port, to provide images of a surgical site inside the patient's body, for example, inside the patient's thoracic cavity. As illustrated in FIG. 1, the patient is shown laying on operating table 40 with laparoscope 30 and surgical tool 55 positioned for insertion into the patient's body. Surgical tool 55 may be any surgical tool usable during laparoscopic surgery, including cutting tools, suction tools, biopsy tools, resection tools, graspers, ablation tools, ligation tools, surgical staplers, ultrasonic and/or electrosurgical vessel sealers, etc.

EM tracking system 70 may be a six degrees-of-freedom EM tracking system, e.g., similar to those disclosed in U.S. Pat. No. 6,188,355 and published PCT Application Nos. WO 00/10456 and WO 01/67035, entitled "WIRELESS SIX-DEGREE-OF-FREEDOM LOCATOR", filed on Dece. 14, 1998 by Gilboa, the entire contents of each of which is incorporated herein by reference, or any other suitable positioning measuring system, is utilized for performing tracking, although other configurations are also contemplated.

EM tracking system 70 may be configured for use with laparoscope 30 to track the position of an EM sensor 94 as it moves in conjunction with laparoscope 30 about the patient's body, as detailed below.

EM tracking system 70 includes a tracking module 72, a plurality of reference sensors 74, and an EM field generator 76. As shown in FIG. 1, EM field generator 76 is positioned beneath the patient. EM field generator 76 and the plurality of reference sensors 74 are interconnected with tracking module 72, which derives the location of each reference sensor 74 in the six degrees of freedom. One or more of reference sensors 74 are attached to the chest of the patient. The six degrees of freedom coordinates of reference sensors 74 are sent as data to computing device 80, which includes an application 81, where the data from sensors 74 are used to calculate a patient coordinate frame of reference.

Laparoscope 30 further includes, or has coupled thereto, at least one EM sensor 94 trackable by tracking module 72. The location of EM sensor 94, and thus the distal end of laparoscope 30, within an EM field generated by EM field generator 76 can be derived by tracking module 72 and computing device 80. Surgical tool 55 may also include, or have coupled thereto, one or more EM sensors 94 to be tracked by tracking module 72 and computing device 80, similar to laparoscope 30.

Computing device 80 includes various software and/or hardware components, such as application 81. As shown in the exemplary embodiment of FIG. 4, computing device 80 may include memory 502, one or more processors 504, a display 506, a network interface 508, an input device 510, and/or an output module 512. Memory 502 may store application 81 and/or image data 514. Application 81 may include instructions which, when executed by processor 504, cause display 506 to present a user interface 516. Application 81 may also provide the interface between the sensed position of EM sensor 94 and the image and planning data developed in the pathway planning phase.

Figure 4:
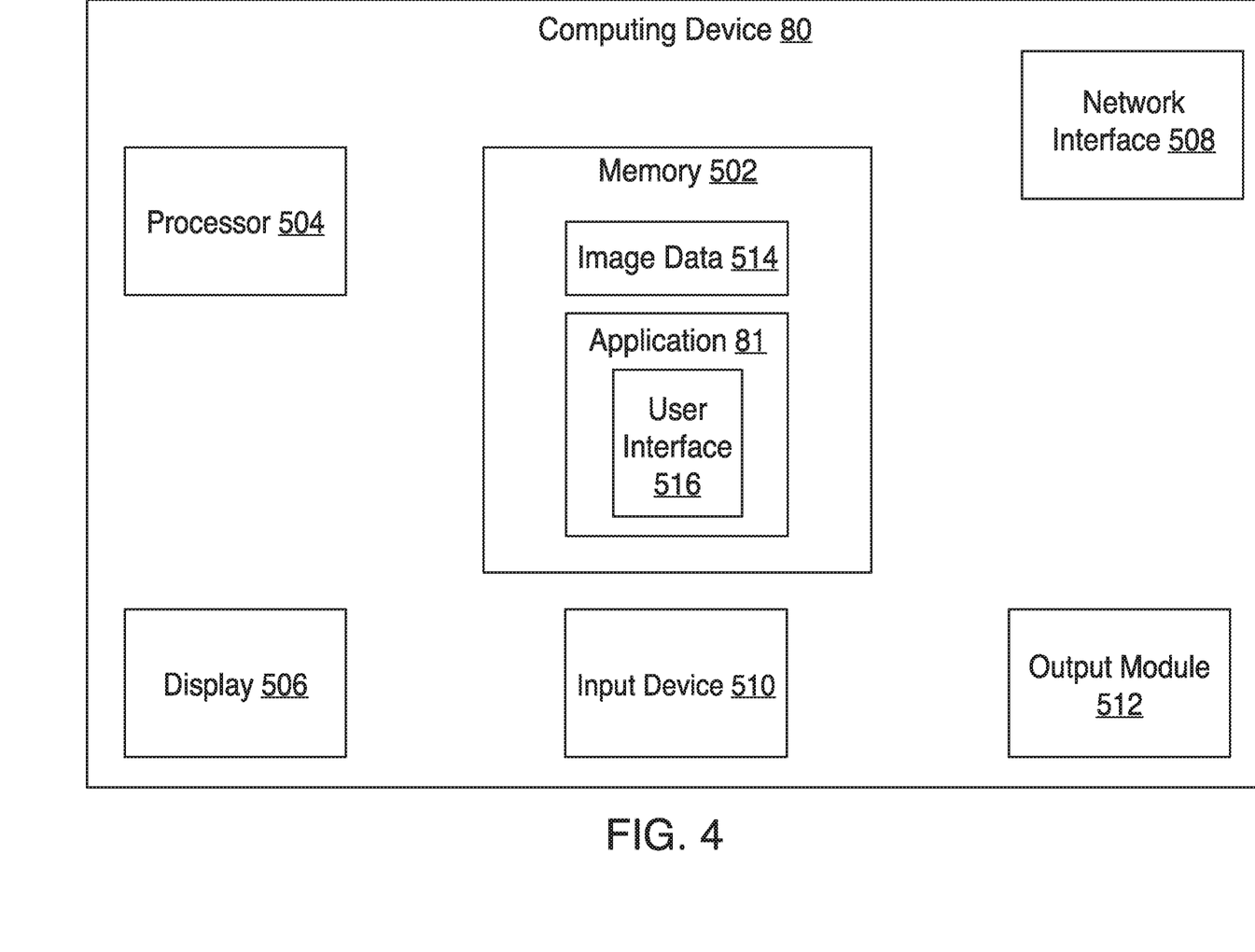
FIG. 4 is a diagram of an example computing device forming part of the system of FIG. 1, according to an embodiment of the present disclosure.

Memory 502 may include any non-transitory computer-readable storage media for storing data and/or software that is executable by processor 504 and which controls the operation of computing device 80. In an embodiment, memory 502 may include one or more solid-state storage devices such as flash memory chips. Alternatively, or in addition to the one or more solid-state storage devices, memory 502 may include one or more mass storage devices connected to the processor 504 through a mass storage controller (not shown) and a communications bus (not shown). Although the description of computer-readable media included herein refers to solid-state storage, it should be appreciated by those skilled in the art that computer-readable storage media may be any available media that is accessable by processor 504. That is, computer readable storage media may include non-transitory, volatile and non-volatile, removable and non-removable media implemented in any method or technology for storage of information, such as computer-readable instructions, data structures, program modules, and/or other data. For example, computer-readable storage media may include RAM, ROM, EPROM, EEPROM, flash memory and/or other solid state memory technology, CD-ROM, DVD, Blu-Ray and/or other optical storage, magnetic cassettes, magnetic tape, magnetic disk storage and/or other magnetic storage devices, and/or any other medium which may be used to store the desired information and is accessable by computing device 80.

Network interface 508 may be configured to connect to a network such as a local area network (LAN) consisting of a wired network and/or a wireless network, a wide area network (WAN), a wireless mobile network, a Bluetooth network, and/or the internet. Input device 510 may be any device by means of which a user may interact with computing device 80, such as, for example, a mouse, keyboard, foot pedal, touch screen, and/or voice interface. Output module 512 may include any connectivity port or bus, such as, for example, parallel ports, serial ports, universal serial busses (USB), or any other similar connectivity port known to those skilled in the art.

Application 81 may be used to facilitate the various phases of the medical procedure, including generating the aforementioned 3D model, and navigating laparoscope 30 and/or treatment tool 55 to the treatment location. For example, computing device 80 utilizes medical image data, such as radiographically obtained computed tomographic (CT), magnetic resonance imaging (MRI), and/or positron emission tomography (PET) image data for generating and viewing the 3D model of the patient's body. While the aforementioned, or any other medical image data known to those skilled in the art, may be used, either individually and/or in combination, the present disclosure will use an CT image data as an example. The 3D model may be displayed on a display monitor associated with computing device 80, for example, display 506, and/or in any other suitable fashion.

Using computing device 80, various views of the 3D model may be displayed and may be manipulated by a clinician to give the clinician a preferred view of the treatment location. As noted above, the treatment location may be a surgical site where the treatment is to be performed. In embodiments where the treatment location is in or adjacent to the patient's lungs, the 3D model may include, among other things, a model airway tree corresponding to the actual airways of the patient's lungs, and showing the various passages, branches, and bifurcations of the patient's actual airway tree. Additionally, the 3D model may include lesions, markers, blood vessels and vascular structures, lymphatic vessels and structures, organs, other physiological structures, and/or a 3D rendering of the pleura and fissures of the lungs. Some or all of the aforementioned elements may be selectively displayed, such that the clinician may choose which elements should be displayed when viewing the 3D model. For example, application 81 may be configured in various states to display the 3D model in a variety of view modes. For each view of the 3D model, the angle from which the 3D model is displayed may correspond to a view point. The view point may be fixed at a predefined location and/or orientation, or may be adjusted by application 81 and/or the clinician operating computing device 80.

As noted above, the systems and methods described in the present disclosure may be used during various medical procedures, including diagnostic and/or treatment procedures performed on various parts and/or organs of the patient's body, such as the lungs, kidneys, spleen, prostate, thyroid, liver, etc. However, for purposes of brevity, the exemplary embodiments described below use the patient's lungs as an example. This is not intended to be limiting, as those skilled in the art will recognize that the same or similar systems and methods as described in the present disclosure may be used during medical procedures performed on various other parts and/or organs of the patient's body.

As an initial step of the procedure, the 3D model is registered with the patient's body. This is required because the position of the patient when the CT image data was obtained often does not correspond to the typical position of the patient during a medical procedure. First, an orientation of the patient is identified in the EM field. A camera, such as laparoscopic camera 35 included in laparoscope 30 along with EM sensor 94, is then used to scan the thoracic area of the patient, typically oriented in a lateral decubitus position. Key information determined from this scan would be the angular rotation of the sagittal plane from the vertical and the curvature or elongation of the chest wall prior to draping the patient. The curvature or elongation of the chest wall is detected by image matching algorithms looking for similar structures near the axilla or scapula and the lower extent of the rib cage. This key information may also be approximated by manual input from the clinician, such as via input device 510. This information is particularly important if any portion of the lung anatomy is simulated, as the orientation relative to gravity must be defined. Once laparoscope 30 is inserted into the patient, the interior of the thoracic cavity is scanned in near entirety by navigating laparoscope 30 about the patient's body. Images captured by laparoscopic camera 35, in coordination with location information detected based on EM sensor 94, may be used to construct a 3D surface image of the anatomic structure including the patient's thoracic cavity and lungs. This may be performed by any number of means of stitching the images into a 3D surface model, such as 2D image triangulation, time of flight, and/or projected/structured light scans. The surface model is then compared with the 3D model constructed from the CT imaging of the lung. Edge finding algorithms may be used to compare the various landmarks in the scanned and CT constructed 3D models which may then be used to align the position of those landmarks in the 3D model with the position in the patient's body, thereby completing the initial registration.

Various other registration processes may also be used to register the 3D model with the patient's body. Examples of such registration processes are described in commonly-owned U.S. Patent Application Publication No. 2011/0085720, entitled "AUTOMATIC REGISTRATION TECHNIQUE," filed on May 14, 2010, by Barak et al., and U.S. Patent Publication No. 2016/0000356, entitled "REAL-TIME AUTOMATIC REGISTRATION FEEDBACK", filed on Jul. 2, 2015, by Brown et al., the contents of each of which are incorporated herein by reference. While the registration process focuses on aligning the patient's body with the 3D model, registration also ensures that the position of airways, vascular structures, pleura, and fissures of the lungs are accurately determined.

In addition to EM tracking system 70, laparoscope 30 and/or surgical tool 55 may also be visualized by using ultrasound imaging. An ultrasound sensor (not shown), such as an ultrasound wand, may be used to image the patient's body during the medical procedure to visualize the location of laparoscope 30 and/or surgical tool 55 inside the patient's body. The ultrasound sensor may have an EM tracking sensor embedded within or attached to the ultrasound wand, for example, a clip-on sensor or a sticker sensor. The ultrasound sensor may be positioned in relation to laparoscope 30 or surgical tool 55 such that laparoscope 30 or surgical tool 55 is at an angle to the ultrasound image plane, thereby enabling the clinician to visualize the spatial relationship of laparoscope 30 or surgical tool 55 with the ultrasound image plane and with objects being imaged. Further, EM tracking system 70 may also track the location of the ultrasound sensor. In some embodiments, one or more ultrasound sensors may be placed inside the patient's body. EM tracking system 70 may then track the location of such ultrasound sensors and laparoscope 30 and/or surgical tool 55 inside the patient's body. An ultrasound workstation may be used to configure, operate, and view images captured by the ultrasound sensor. Objects such as the target surgical lesion or anatomic features even in the chest wall may be used as landmarks for systematic registration of the scanned and CT generated 3D models.

Figure 2:
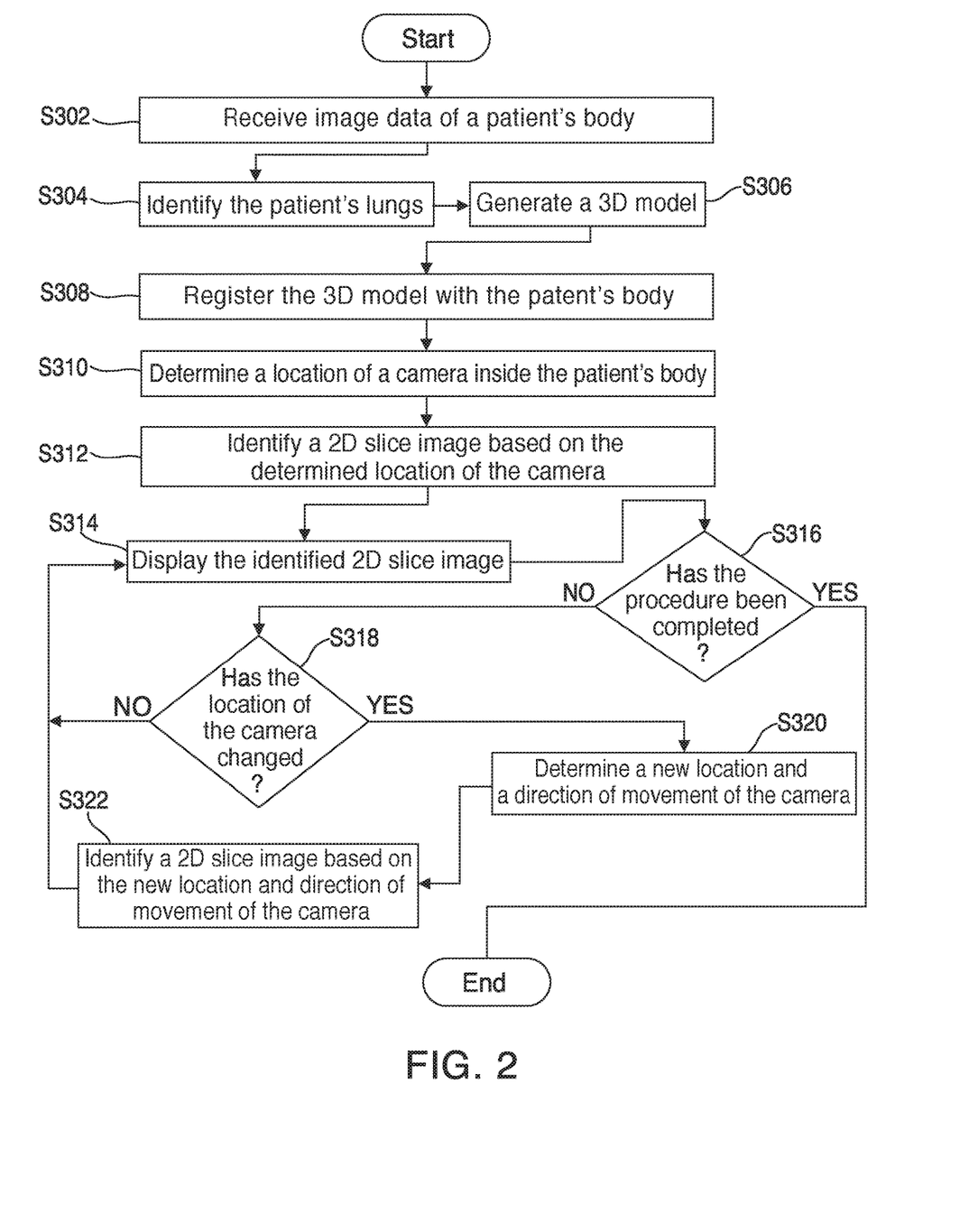
FIG. 2 shows a flowchart of an example method for controlling a medical image viewer based on movement of surgical tools, according to an embodiment of the present disclosure.

Turning now to FIG. 2, there is shown a flowchart of an exemplary method of controlling images displayed by a medical image viewer based on movement of surgical tools, in accordance with an embodiment of the present disclosure. The method described below details an exemplary embodiment wherein laparoscopic thoracic surgery is performed. However, those skilled in the art will appreciate that the same or similar steps to those described below may also be used in various other medical procedures and/or settings.

Starting at step S302, computing device 80 receives image data of the patient's body. The image data may be collected by one or more of various imaging modalities, including computed tomography (CT) scans, cone beam computed tomography (CBCT) scans, magnetic resonance imaging (MRI) scans, positron emission tomography (PET) scans, ultrasound scans, X-ray scans, and/or any other relevant imaging modality known to those skilled in the art. The image data may be received in, or converted to, a uniform data format, such as the digital imaging and communications in medicine (DICOM) standard. For example, the patient may undergo a CT scan prior to the medical procedure during which CT image data of at least a portion of the patient's body is collected and compiled into a CT scan volume. The CT scan volume may include 2D slice images of the patient's body in axial, sagittal, and coronal orientations, and may further be processed to generate 2D slice images in various other orientations.

Next, at step S304, application 81 processes the received image data to identify landmarks and/or structures, such as the patient's lungs, in the image data. The image processing may include automatic and/or user-assisted image analysis to identify the patient's lungs in the image data. Various image processing methods may be used, including region growing techniques, as described in in co-pending U.S. Patent Application Publication No. 2016/0038248, entitled "TREATMENT PROCEDURE PLANNING SYSTEM AND METHOD", filed on Aug. 10, 2015, by Bharadwaj et al., and co-pending U.S. Patent Application Publication No. 2016/0005193, entitled "SYSTEM AND METHOD FOR SEGMENTATION OF LUNG", filed on Jun. 30, 2015, by Markov et al., the contents of both of which are incorporated herein by reference.

Thereafter, at step S306, application 81 generates a three-dimensional (3D) model of the patient's lungs. The 3D model includes graphical representations of the patient's lungs, showing the locations of the lumens of the bronchial, vascular, and lymphatic trees, as well as the fissures and pleura of the patient's lungs. Application 81 may also generate an inflated and/or deflated 3D model of the patient's lungs wherein inflation and/or deflation of some or all areas of the patient's lungs is simulated, based on the needs of the particular surgical procedure being performed.

At step S308, the 3D model is registered with the patient's body. As described above, when using system 100, registration may involve moving laparoscope 30 including EM sensor 94 about the patient's thoracic cavity, tracking the location of EM sensor 94 during such movement, and iteratively updating the 3D model based on the tracked location of EM sensor 94 by comparing the landmarks found in the scanned and CT constructed 3D models to register the two models with each other, as further described above.

Thereafter, at step S310, the location, orientation, and direction of movement of one or more tools is determined. As used herein the term "tool" refers to any instrument inserted into the patient's body which may have an EM sensor 94 attached thereto or incorporated therein. The clinician may select, at the start of the procedure or during the procedure, which EM sensor 94, and thus which tool, should be used for identifying a medical image to be displayed. In the exemplary embodiment described here, the tool is laparoscope 30 which includes laparoscopic camera 35, as described above with reference to FIG. 1. In another embodiment, the tool is a vessel sealer or surgical stapler, such as surgical tool 55. Further, as described above, the tool includes an EM sensor 94 enabling an EM tracking system 70 to detect the location of the tool inside the patient's body. By tracking successive locations of EM sensor 94, an orientation and direction of movement of the tool may also be determined.

In embodiments where system 100 includes a surgical robot, the tool, e.g. laparoscope 30 or surgical tool 55, may be coupled to one or more robotic arm assemblies. In such embodiments, the location, orientation, and direction of movement of the tool may be determined based on a pose of the surgical robot. The pose of the surgical robot corresponds to the particular location and orientation of each component of the surgical robot at a particular point in time. For example, the controller operating the surgical robot will know the location, orientation, and direction of movement of the various components of the surgical robot, including the tools coupled thereto. As such, the location, orientation, and direction of movement of any tools coupled to the surgical robot may be determined based on the location, orientation, and direction of movement of the various components of the surgical robot.

At step S312, application 81 may identify and select a medical image, such as a 2D slice image, based on the determined location of the tool. For example, the 2D slice image may be a CT image from a CT image volume, such as the image data received at step S302. Alternatively, the 2D slice image may be a 2D image generated based on the 3D model. In embodiments, the 2D slice image is generated based on the image data received at step S302 in a non-orthogonal orientation. That is, the 2D slice image is generated in an orientation different from the axial, saggital, and coronal orientations. Application 81 may then, at step S314, cause a display device, such as display 506 (FIG. 4) to display the 2D slice image, as shown in FIG. 3 (described below).

Next, at step S316, application 81 determines whether the medical procedure has been completed. For example, application 81 may receive input from the clinician and/or may determine, based on the detected location of the tools, that the procedure is complete, and thereby end the process. However, if application 81 determines that the procedure is not complete, processing continues to step S318, where application 81 determines whether the location of the tool has changed. If the location of the tool has not changed, processing returns to step S314 where the same 2D slice image previously identified is displayed. However, if application 81 determines that the location of the tool has changed, processing proceeds to step S320, where application 81 determines a new location, orientation, and direction of movement of the tool.

Thereafter, at step S322, application 81 identifies a new 2D slice image based on the new location, orientation, and direction of movement of the tool. For example, the new 2D slice image may generated based on the image data received at step S302. In embodiments, the direction of movement of the tool is non-orthogonal, that is, the direction of movement of the tool is not along the axial, saggital, or coronal axes. In such embodiments, the new 2D slice image may be generated in a non-orthogonal orientation. That is, the 2D slice image is generated in an orientation different from the axial, saggital, and coronal orientations. Processing then returns to step S314 where the newly identified 2D slice image is displayed. Steps S314 to S322 may be repeated until such time that application 81 determines at step S316 that the procedure is complete.

Figure 3:
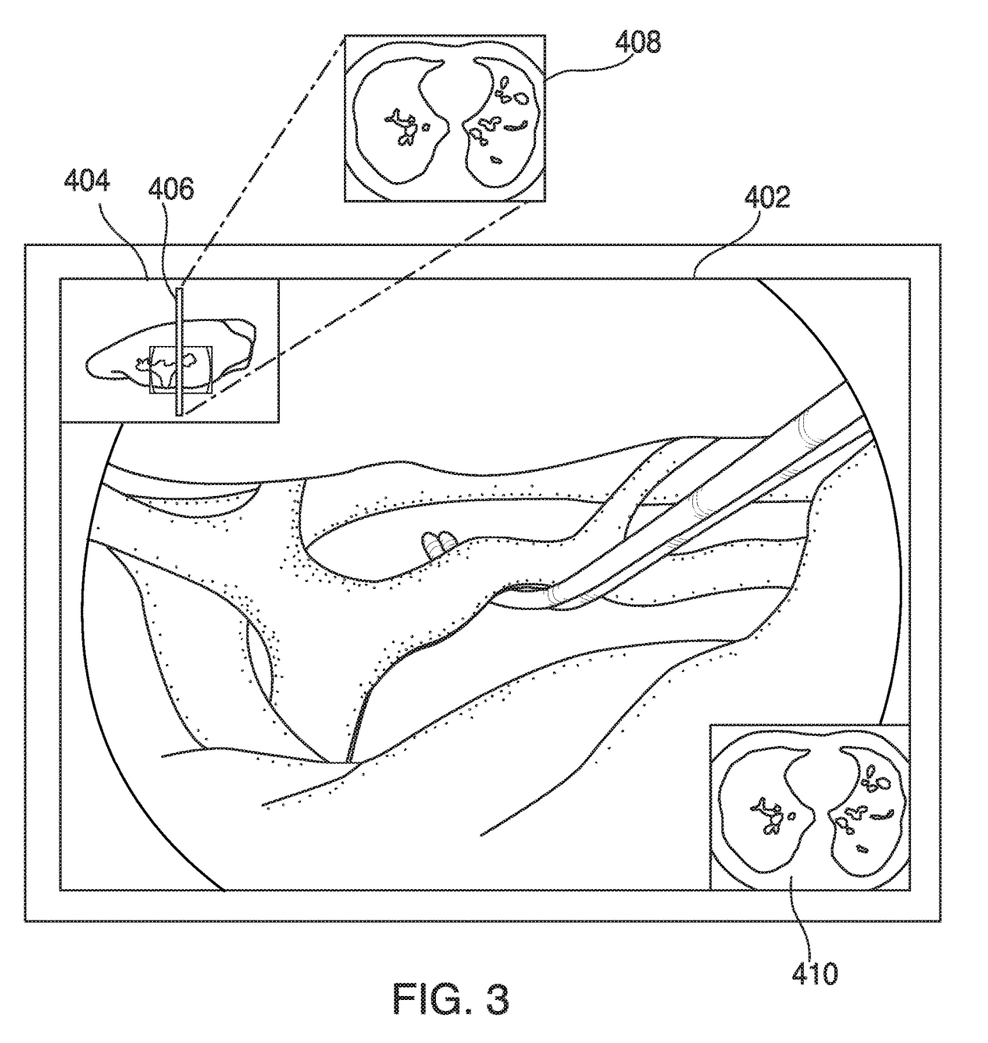
FIG. 3 is an exemplary user interface which may be displayed by a display device forming part of the system of FIG. 1, according to an embodiment of the present disclosure.

FIG. 3 shows an example view of the medical image viewer which may be displayed by the display device. The medical image viewer may include a live view 402 from a camera, such as laparoscopic camera 35, inserted in the patient's body, a view 404 of the 3D model including a line 406 on the view 404 of the 3D model which indicates the position and orientation of a slice image 408. Slice image 408 may be in a view 410 of the slice image 408, such as a "picture in picture" or an overlay over live view 402. View 404 of the 3D model and slice image 408 may selectively be displayed and/or disabled based on the procedure and the clinician's preferences.

Detailed embodiments of devices, systems incorporating such devices, and methods of using the same are described herein. However, these detailed embodiments are merely examples of the disclosure that may be embodied in various forms. Therefore, specific structural and functional details disclosed herein are not to be interpreted as limiting, but merely as a basis for the claims and as a representative basis for allowing one skilled in the art to variously employ the present disclosure in appropriately detailed structure. While the preceding embodiments are described in terms of a patient's lungs, those skilled in the art will realize that the same or similar devices, systems, and methods may be used in other parts of the patient's body as well.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method of displaying medical images based on a location of a laparoscopic camera, the method comprising:
    receiving image data of a patient's body prior to a medical procedure;
    generating a three-dimensional (3D) model of at least a portion of the patient's body based on the image data;
    registering the 3D model with the patient's body;
    determining a location of the laparoscopic camera inside the patient's body during the medical procedure;
    determining, based on the location of the laparoscopic camera and one or more further locations of the laparoscopic camera, a direction of movement of the laparoscopic camera within the patient's body along an axis that is not an axial axis, a sagittal axis, or a coronal axis of the patient's body;
    selecting from the 3D model, based on the determined direction of movement of the laparoscopic camera, a 2D slice image of inside the patient's body at the determined location of the laparoscopic camera in an orientation that corresponds to the determined direction of movement of the laparoscopic camera; and
    displaying, on a single display screen during the medical procedure:
        the selected 2D slice image overlaid on a live view from inside the patient's body captured by the laparoscopic camera;
        the 3D model overlaid on the live view; and
        a line overlaid on the display of the 3D model to indicate a location on the displayed 3D model from where the 2D slice image was selected.

2. The method according to claim 1, wherein the laparoscopic camera is coupled to an electromagnetic sensor and the location of the laparoscopic camera inside the patient's body is determined based on a tracked position of the electromagnetic sensor inside the patient's body.

3. The method according to claim 1, wherein the laparoscopic camera is coupled to a surgical robot.

4. The method according to claim 3, wherein the location of the laparoscopic camera inside the patient's body is determined based on stored data corresponding to a pose of the surgical robot.

5. A method of displaying medical images based on a location of a laparoscopic camera during a medical procedure, the method comprising:
    receiving image data of a patient's body prior to a medical procedure;
    generating a three-dimensional (3D) model of at least a portion of the patient's body based on the image data;
    registering the 3D model with the patient's body;

determining, based on the location of the laparoscopic camera and one or more further locations of the laparoscopic camera, a direction of movement of the laparoscopic camera within the patient's body along an axis that is not an axial axis, a sagittal axis, or a coronal axis of the patient's body;

selecting from the 3D model, based on the determined direction of movement of the laparoscopic camera, a 2D slice image of inside the patient's body at the determined location of the laparoscopic camera in an orientation that corresponds to the determined direction of movement of the laparoscopic camera; and displaying, on a single display screen during the medical procedure:
- the selected 2D slice image overlaid on a live view from inside the patient's body captured by the laparoscopic camera;
- the 3D model overlaid on the live view; and
- a line overlaid on the display of the 3D model to indicate a location on the displayed 3D model from where the 2D slice image was selected.

* * * * *